United States Patent [19]

Charlton et al.

[11] Patent Number: 5,714,389
[45] Date of Patent: Feb. 3, 1998

[54] TEST DEVICE AND METHOD FOR COLORED PARTICLE IMMUNOASSAY

[75] Inventors: David E. Charlton, Allentown, N.J.; Neal W. Miller, Lebanon, Pa.

[73] Assignee: Carter-Wallace, Inc., New York, N.Y.

[21] Appl. No.: 995,331

[22] Filed: Dec. 23, 1992

Related U.S. Application Data

[63] Continuation of Ser. No. 702,450, May 16, 1991, abandoned, which is a continuation of Ser. No. 211,582, Jun. 27, 1988, abandoned.

[51] Int. Cl.$^6$ ................................................ G01N 33/558
[52] U.S. Cl. .................... 436/514; 435/970; 436/501; 436/515; 436/518; 436/523; 436/524; 436/525; 436/814; 436/817; 436/818
[58] Field of Search ........................... 436/514, 518, 436/523, 524, 525, 533, 544, 169, 178, 810, 814, 817, 818, 501, 515; 435/176, 7.92, 970; 422/56, 55, 57; 427/2

[56] References Cited

U.S. PATENT DOCUMENTS

| | | |
|---|---|---|
| 3,620,677 | 11/1971 | Morison . |
| 3,811,840 | 5/1974 | Bauer et al. . |
| 3,888,629 | 6/1975 | Bagshawe . |

(List continued on next page.)

FOREIGN PATENT DOCUMENTS

| | | | |
|---|---|---|---|
| A 63502/86 | 10/1986 | Australia ........................ | 436/518 |
| 0007654 | 2/1980 | European Pat. Off. ............ | 436/525 |
| 0018561 | 11/1980 | European Pat. Off. . | |
| 0032270 | 7/1981 | European Pat. Off. ............ | 436/525 |
| 0063810 | 11/1982 | European Pat. Off. ............ | 436/518 |
| 0088636 | 9/1983 | European Pat. Off. ............ | 436/518 |
| 0154749 | 12/1984 | European Pat. Off. . | |
| 0 183 442 A2 | 6/1985 | European Pat. Off. . | |
| 0 149 168 A1 | 7/1985 | European Pat. Off. . | |

(List continued on next page.)

OTHER PUBLICATIONS

Collins. H.W.P., "Alternative Immunoassays", Ed. John Wiley & Sons, 1985 pp. 34–57.

Surek, B. "Visualization of Antigenic Proteins Blotted onto Nitrocellulose Using The Immuno–Gold Staining (IGS) Method" Biochemical and Biophysical Research Communications, 121 (1), 284–289, 1984.

Hsu, Y.-H., "Immunogold for Detection of Antigen on Nitrocellulose Paper" Anal. Biochem., 142, 221–225, 1984.

Puissieux, F et al., "Les Liposomes; Applications Therapeutiques"Technique et Documentation (Lavoisier) 1985, Ch. 2, p. 48 (French, with translation).

Chemical Abstract 5: 3753 Titled: 1. "The capillary Analysis of Colloid Solutions" F. Fichter and N. Sahlbom, Verhandl, Naturforsch. Ges. Basel 21, 1–24; Chem. Zentr., 1910, II, 1088. 2. The Capillary Electric Precipitation of Positive Colloids F. Fichter; Z. Chem. Ind. Kolloide, 8 pp. 1–2 (1911).

Brdicka, R., "*Grundlagen Der Physikalischen Chemie*", Ch. X, pp. 774–775 and 784–787; Veb. Deutscher Verlag Der Wissenschaften, Berlin (1958), in German—no translation.

(List continued on next page.)

*Primary Examiner*—Carol A. Spiegel
*Attorney, Agent, or Firm*—Testa, Hurwitz & Thibeault, LLP

[57] ABSTRACT

Disclosed is a test cell and a method for detection of a preselected ligand in a liquid sample such as a body fluid. The test cell includes an elongate outer casing which houses an interior permeable material capable of transporting an aqueous solution and defining a sample inlet, a test volume, and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site which includes a first protein having a binding site specific to a first epitope of the ligand immobilized in fluid communication with the flow path. The test site can be observed through a window of the casing.

10 Claims, 2 Drawing Sheets

U.S. PATENT DOCUMENTS

| | | | |
|---|---|---|---|
| 4,042,335 | 8/1977 | Clement . | |
| 4,045,384 | 8/1977 | Dorman . | |
| 4,094,647 | 6/1978 | Deutsch et al. . | |
| 4,168,146 | 9/1979 | Grubb et al. . | |
| 4,169,138 | 9/1979 | Jonsson . | |
| 4,205,952 | 6/1980 | Cais . | |
| 4,219,335 | 8/1980 | Ebersole . | |
| 4,235,601 | 11/1980 | Deutsch et al. | 436/514 X |
| 4,256,834 | 3/1981 | Zuk et al. . | |
| 4,258,001 | 3/1981 | Pierce et al. . | |
| 4,294,818 | 10/1981 | McMichael et al. . | |
| 4,297,344 | 10/1981 | Schwinn et al. . | |
| 4,313,734 | 2/1982 | Leuvering . | |
| 4,348,207 | 9/1982 | Cappel . | |
| 4,357,142 | 11/1982 | Schall, Jr. et al. . | |
| 4,361,537 | 11/1982 | Deutsch et al. | 422/56 |
| 4,366,241 | 12/1982 | Tom et al. . | |
| 4,373,932 | 2/1983 | Gribnau et al. | 436/501 |
| 4,376,110 | 3/1983 | David et al. | 436/513 |
| 4,411,518 | 10/1983 | Meserol et al. . | |
| 4,419,453 | 12/1983 | Dorman et al. | 436/534 |
| 4,434,150 | 2/1984 | Azad et al. . | |
| 4,435,504 | 3/1984 | Zuk et al. | 436/514 X |
| 4,446,232 | 5/1984 | Liotta . | |
| 4,459,358 | 7/1984 | Berke | 436/170 |
| 4,477,575 | 10/1984 | Vogel et al. | 422/56 |
| 4,486,530 | 12/1984 | David et al. . | |
| 4,487,839 | 12/1984 | Kamentsky | 436/518 |
| 4,496,654 | 1/1985 | Katz et al. . | |
| 4,503,143 | 3/1985 | Gerber et al. . | |
| 4,508,829 | 4/1985 | Sulitzeanu | 436/510 |
| 4,515,889 | 5/1985 | Klose et al. | 435/4 |
| 4,537,861 | 8/1985 | Elings et al. | 436/518 |
| 4,552,839 | 11/1985 | Gould et al. | 435/7.9 |
| 4,590,169 | 5/1986 | Cragle et al. | 436/523 |
| 4,594,327 | 6/1986 | Zuk | 436/514 |
| 4,604,364 | 8/1986 | Kosak | 436/501 |
| 4,623,461 | 11/1986 | Hossom et al. | 210/445 |
| 4,624,929 | 11/1986 | Ullman | 436/179 |
| 4,632,901 | 12/1986 | Valkirs et al. | 435/5 |
| 4,639,242 | 1/1987 | Babson . | |
| 4,639,419 | 1/1987 | Olson et al. | 435/5 |
| 4,647,544 | 3/1987 | Nicoli et al. | 436/518 |
| 4,654,309 | 3/1987 | Milnar et al. | 422/56 |
| 4,665,034 | 5/1987 | Chandler | 435/287 |
| 4,690,907 | 9/1987 | Hibino et al. | 436/514 |
| 4,703,017 | 10/1987 | Campbell et al. | 436/501 |
| 4,756,828 | 7/1988 | Litman et al. | 435/7.9 |
| 4,757,004 | 7/1988 | Houts et al. | 435/7.9 |
| 4,761,381 | 8/1988 | Blatt et al. | 436/165 |
| 4,770,853 | 9/1988 | Bernstein | 422/58 |
| 4,772,550 | 9/1988 | Greenquist | 435/7.9 |
| 4,774,192 | 9/1988 | Terminiello et al. | 436/540 |
| 4,778,751 | 10/1988 | El Shami et al. | 435/7.9 |
| 4,803,170 | 2/1989 | Stanton et al. | 436/518 |
| 4,806,311 | 2/1989 | Greenquist | 422/56 |
| 4,806,312 | 2/1989 | Greenquist | 422/56 |
| 4,853,335 | 8/1989 | Olsen et al. | 436/527 |
| 4,857,453 | 8/1989 | Ullman et al. . | |
| 4,859,612 | 8/1989 | Cole et al. | 436/523 |
| 4,861,711 | 8/1989 | Friesen et al. . | |
| 4,868,108 | 9/1989 | Bahar et al. | 435/7.9 |
| 4,883,688 | 11/1989 | Houts et al. | 427/285 |
| 4,891,313 | 1/1990 | Berger et al. | 436/7 |
| 4,916,056 | 4/1990 | Brown, III et al. . | |
| 4,920,046 | 4/1990 | McFarland et al. . | |
| 4,945,042 | 7/1990 | Geiger et al. . | |
| 4,956,302 | 9/1990 | Gordon et al. | 436/161 |
| 4,960,691 | 10/1990 | Gordon et al. | 435/6 |
| 4,962,023 | 10/1990 | Todd et al. . | |
| 4,963,468 | 10/1990 | Olson . | |
| 4,981,785 | 1/1991 | Nayak . | |
| 4,981,786 | 1/1991 | Dafforn et al. | 422/56 |
| 4,985,204 | 1/1991 | Klose et al. | 422/56 |
| 4,999,285 | 3/1991 | Stiso | 435/7.9 |
| 5,006,474 | 4/1991 | Horstman et al. | 422/56 |
| 5,008,080 | 4/1991 | Brown, III et al. | 422/56 |
| 5,030,558 | 7/1991 | Litman et al. | 435/7.91 |
| 5,039,607 | 8/1991 | Skold et al. | 435/7.5 |
| 5,043,428 | 8/1991 | Heimburger et al. | 530/383 |
| 5,075,078 | 12/1991 | Osikowicz et al. | 422/56 |
| 5,120,504 | 6/1992 | Petro-Roy et al. | 422/58 |
| 5,120,643 | 6/1992 | Ching et al. | 435/7.92 |
| 5,141,850 | 8/1992 | Cole et al. | 436/525 |
| 5,141,875 | 8/1992 | Kelton et al. | 436/514 |
| 5,156,952 | 10/1992 | Litman et al. | 435/7.91 |
| 5,164,294 | 11/1992 | Skold et al. | 435/7.5 |
| 5,232,835 | 8/1993 | Litman et al. | 435/7.93 |
| 5,248,619 | 9/1993 | Skold et al. | 436/514 |
| 5,591,645 | 1/1997 | Rosenstein | 436/514 |
| 5,602,040 | 2/1997 | May et al. | 436/514 |
| 5,622,871 | 4/1997 | May et al. | 436/514 |
| B1 4,366,241 | 10/1988 | Tom et al. . | |

FOREIGN PATENT DOCUMENTS

| | | | |
|---|---|---|---|
| 0154749 | 9/1985 | European Pat. Off. | 436/518 |
| 0158746 | 10/1985 | European Pat. Off. | 436/525 |
| 0164180 | 12/1985 | European Pat. Off. | 436/518 |
| 0 170 746 A1 | 2/1986 | European Pat. Off. . | |
| 0 217 403 A2 | 3/1986 | European Pat. Off. . | |
| 0186799 | 7/1986 | European Pat. Off. | 435/7.9 |
| 0 191 640 A2 | 8/1986 | European Pat. Off. . | |
| 192 320 | 8/1986 | European Pat. Off. . | |
| 0201079 | 11/1986 | European Pat. Off. | 435/7.5 |
| 0 212 603 | 3/1987 | European Pat. Off. . | |
| 0 225 054 | 6/1987 | European Pat. Off. . | |
| 0 225 054 A1 | 6/1987 | European Pat. Off. . | |
| 0 258 963 A2 | 8/1987 | European Pat. Off. . | |
| 0 250 137 A2 | 12/1987 | European Pat. Off. . | |
| 0 258 963 | 3/1988 | European Pat. Off. . | |
| 0271204A2 | 6/1988 | European Pat. Off. . | |
| 0284232 A1 | 9/1988 | European Pat. Off. | 436/518 |
| 0291194 | 11/1988 | European Pat. Off. | 436/518 |
| 0299428 A2 | 1/1989 | European Pat. Off. | 435/7.92 |
| 0306336 | 3/1989 | European Pat. Off. | 436/518 |
| 0337082 | 10/1989 | European Pat. Off. | 435/7.5 |
| 0349215 | 1/1990 | European Pat. Off. | 436/518 |
| 0320240 B1 | 3/1991 | European Pat. Off. | 435/6 |
| 0420021A1 | 4/1991 | European Pat. Off. . | |
| 212599 B1 | 10/1991 | European Pat. Off. | 422/56 |
| 0505636A1 | 9/1992 | European Pat. Off. . | |
| 0560410 A2 | 9/1993 | European Pat. Off. | 436/518 |
| 0560411 A2 | 9/1993 | European Pat. Off. | 436/518 |
| 0284232 B1 | 6/1995 | European Pat. Off. | 436/518 |
| 2356944 | 1/1978 | France . | |
| 3044385 | 6/1982 | Germany . | |
| 3432083 | 3/1986 | Germany . | |
| 8 805 565 | 9/1988 | Germany . | |
| 8703007 | 12/1988 | Netherlands | 436/525 |
| 2 016 687 | 9/1979 | United Kingdom . | |
| 2204398 | 11/1988 | United Kingdom | 436/518 |
| WO 86/03839 | 7/1986 | WIPO . | |
| WO 86/04683 | 8/1986 | WIPO | 435/7.9 |
| WO 87/02774 | 5/1987 | WIPO | 435/7.9 |
| WO 88/05912 | 8/1988 | WIPO | 436/540 |
| WO88/08534 | 11/1988 | WIPO . | |
| WO 91/12528 | 7/1991 | WIPO | 436/525 |

OTHER PUBLICATIONS

Bosch, A.M. G., "Enzym–und Sol Particle Immunoassays für Hormone", Gynecology and Obstetrics, pp. 509–512; 1987, in German + English Summary.

Moeremans, M., et al., "Sensitive Visualization of Antigen–Assays with Immunogold and Immunogold/Silver Staining", J. Immunological Methods, 74, pp. 353–360, 1984.

Maguire, T.A., "Pregnancy and Ovulation Testing"; The Pharmaceutical Journal, 531–533, (1989), May 6.

Chard, T., "Pregnancy Tests: A Review", Human Reproduction, vol. 7, No. 5, pp. 701–710, 1952.

Bredig–Leipzig, "Einige Anwendungen Des Elektrischen Lichtbogens", Zeitschrist Für Electrochemie, Heft. 22, pp. 514–515; (1898), in German + English Summary.

Wiberg, E., "Lehrbuch Der Anorganischen Chemie", pp. 333–338, Walter De Gruyter & Co., Berlin, 1960, in German + English Summary.

Unanue, E.R., Benacerraf, B.; "Immunfluoreszenz"; Immunologie, pp. 63–65; Walter de Gruyter, Berlin–New York 1987, in German + full English translation.

Wright, J.F.; "A Simple Immunodiagnostic Test System for Alternate Site Market"; World Biotech Report, pp. 263–271; 1988.

Zsigmondy, R.; "Ueber Wassrige Lösungen Metallischer Goldes", Annalen Der Chemie, 301, pp. 29–54; 1898, in German.

Van Hell, H., et al., "Particle Immunoassays"; Alternative Immunoassays, Ch. 4, pp. 39–58; 1985.

Kronick, M.N., "Immunoassay Techniques with Fluorescent Phycobiliprotein Conjugates", Clinical Chemistry, 29/9, 1582–1586, 1983.

"Polar Bear Hits Town; OPUS Immunoassay System", Diagnostic News, issue 1, Mar. 1992, Behring, pp. 1–3.

Stanley, C.J., et al., "Enzyme Amplification Can Enhance Both the Speed and the Sensitivity of Immunoassays", J. Immunological Methods, 83, 89–95 (1985).

Stanley, C.J., et al., "Enzyme Amplification: A New Technique for Enhancing the Speed and Sensitivity of Enzyme Immunoassays", I.C.P.R., 44–51; Jul./Aug. 1985.

Johannsson, A., et al., "A Fast Highly Sensitive Colorimetric Enzyme Immunoassay System Demonstrating Benefits of Enzyme Amplifications in Clinical Chemistry", Clinica Chemica Acta, 148, 119–124, (1985).

Moss, D.W., et al., "An Enzyme–Amplified Monoclonal Immunoenzymometric Assay for Prostatic Acid Phosphatase", Clinica Chimica Acta, 152, 85–94 (1985).

Johannsson, A., et al., "Enzyme Amplification for Immunoassays Detection Limit of One Hundredth of an Attomole", J. Immunological Methods, 87, 7–11 (1986).

Stanley, C.J., et al., "Use of a New and Rapid Milk Progesterone Assay to Monitor Reproductive Activity in the Cow", The Veterinarian Record, Jun. 14, 1986, pp. 664–667.

Heap, R.B., et al., "Mechanisms of Transfer of Steroid Hormones and Growth Factors into Milk", Endocrinologia Experimentals, vol. 20, pp. 101–118; 1986.

Worsfold, A.L., et al., "The Evaluation of a New Rapid Milk Progesterone Test as an Aid to Improving Dairy Herd Fertility", British Veterinary Journal, 143, 83–87, 1987.

Stanley, C.J., et al., "Enzyme–Amplified Immunoassays", J. Pharmaceutical and Biomedical Analysis, vol. 5, No. 8, pp. 811–820, 1987.

Stanley, C.J., et al., "Amperometric Enzyme–Amplified Immunoassays", J. Immunological Methods, 112, 153–161, 1988.

Chemical Abstract 53: 187451 (1959).

Lou et al., One–Step Competitive Immunochromatographic Assay for Semiquantitative Determiniation of Lipoprotein(a) in Plasma, 39(4) Clin. Chem 619–624 (1993).

Ferns, Controlled Nucleation for the Regulation of the Particle Size in Monodisperse Gold Suspension, 241 Nature Physical Science 20–22 (1973).

Gribnau, et al., Particle–Labelled Immunoassays: A Review, 376 J. of Chromatography Biomedical Applications 175–189 (1986).

Leuvering et al., Optimization of a Sandwich Sol Particle Immunoassay for Human Chorionic Gonadotrophin, 62 J.of Immunological Methods 175–184 (1983).

Fichter, Ueber die kapillarelektrische Fällung positiver Kolloide, Zeitschrift Für Chemie Und Industrie Der Kolliode 1–2 (1911) No English Translation.

J. Perrin, Mécanisme de L'Électrisation de Contact et Solutions Colloidales, Tome III J. De Chimie Physique 50–160 (1905) No English Translation.

J. Perrin, Mécanisme de L'Électrisation de Contact et Solutions Colloidales, Tome II. J.De Chimie Physique 601–51 (1904) No English Translation.

Fichter et al., Die Kapillaranalyse Kolloidaler Lösungen, 21 Verhandl Naturfrsch.Ges.Basel 2–24 (1910) No English Translation.

Runge, Die Runft der Farbenbereitung, Farbenchemie (1850) No English Translation.

H. Weil, The Evolution of Paper Chromatography, 132 Kolloid-Z (1953) pp. 149–162.

H. Weil, Der Ursprung der Papierchromatographie, 40 Naturwissenschaften (1953), pp. 1–7 No translation.

V.N. Sahlbom, Kapilaranalyse Kolloider Losugen, 2 kolloidchemische Beihefte (1910–11), pp. 79–141 No translation.

E. Blasius and M. Fischer, Papierchromatographische und papierionophoretische Trennung der Platinelemente und des Goldes, 177 z. Anal. Chem. (1960), pp. 412–420 No translation.

E. Blasius and M. Fischer, Papierchromatographische und papierionophoretische Trennung der Elemente der Reduktionsgruppe, 178 z. Anal. Chem. (1960), pp. 28–33 No translation.

Lederer, M., "Chromatographic Properties of Two Gold Compounds Used in the Therapy of Polyarthritis", 153 Journal of Chromatography, 302–304 (1978).

Colloidal Metal Marking Reference Book (1984–85), vol. 2, No. 1, pp. 1–44.

Zuk et al., Enzyme Immunochromatography—A Quantitative Immunoassay Requiring No Instrumentation, Clinical Chemistry, vol. 31, No. 7, 1985, pp. 1145–1150.

Greenquist et al., "Homogenous Fluorescent Immunoassay with Dry Reagents," Clinical Chemistry, vol. 27, No. 9, 1981.

Frens, "Controlled Nucleation for the Regulation of the Particle Size in Monodisperse Gold Suspensions," 241 Nature Physical Science 20–22 (1973).

Horisberger, "Evaluation of Colloidal Gold as a Cytochromic Marker for Transmission and Scanning Electron Microscopy," 36 Biol. Cellulaire 253–58 (1979).

Leuvering, et al, "Sol Particle Immunoassay (SPIA)," 1 (1) J. Immunoassay 77–91 (1980).

Tijssen, Laboratory Techniques in Biochemistry and Molecular Biology, vol. 15, "Practice and Theory of Enzyme Immunoassays," Chapter 13—The Immobilization of Immunoreactants on Solid Phases, 297–328.

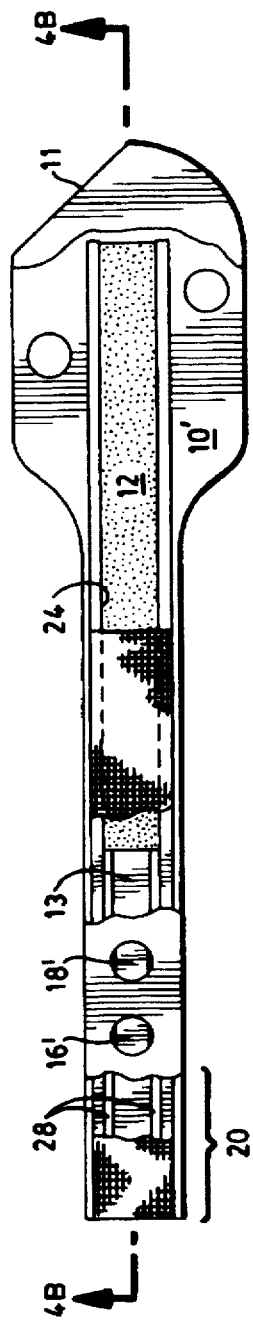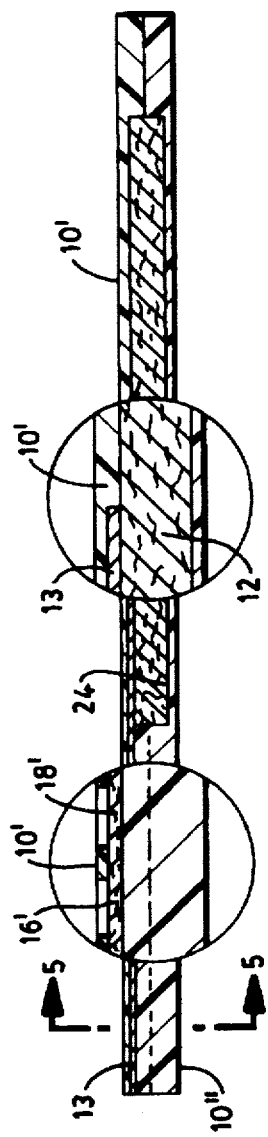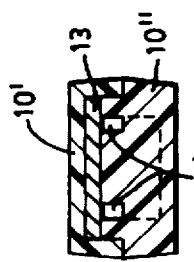

TEST DEVICE AND METHOD FOR COLORED PARTICLE IMMUNOASSAY

This application is a continuation of applications Ser. No. 07/702,450 filed May 16, 1991, now abandoned, which was a continuation of U.S. Ser. No. 07/211,582, filed Jun. 27, 1988, now abandoned.

BACKGROUND OF THE INVENTION

This invention relates to assays for ligands, e.g., antigens, in a liquid sample such as a body fluid. More particularly, the invention relates to a method and apparatus for the detection of a ligand in a body fluid such as urine using a conjugate comprising colored particles and a novel flow-through test cell.

Many types of ligand-receptor assays have been used to detect the presence of various substances, often generally called ligands, in body fluids such as urine. These assays involve antigen antibody reactions, synthetic conjugates comprising radioactive, enzymatic, fluorescent, or visually observable metal sol tags, and specially designed reactor chambers. In all these assays, there is a receptor, e.g., an antibody, which is specific for the selected ligand or antigen, and a means for detecting the presence, and often the amount, of the ligand-receptor reaction product. Most current tests are designed to make a quantitative determination, but in many circumstances all that is required is a positive/negative indication. Examples of such qualitative assays include blood typing and most types of urinalysis. For these tests, visually observable indicia such as the presence of agglutination or a color change are preferred.

Even the positive/negative assays must be very sensitive because of the often small concentration of the ligand of interest in the test fluid. False positives can also be troublesome, particularly with agglutination and other rapid detection methods such as dipstick and color change tests. Because of these problems, sandwich assays and other sensitive detection methods which use metal sols or other types of colored particles have been developed. These techniques have not solved all of the problems encountered in these rapid detection methods.

It is an object of this invention to provide a rapid, sensitive method for detecting ligands in body fluids. Another object is to provide an assay which has high sensitivity and fewer false positives than conventional assays. A further object is to provide a test cell for detection of low levels of ligands in body fluids. Another object is to provide an assay system which involves a minimal number of procedural steps, and yields reliable results even when used by untrained persons.

These and other objects and features of the invention will be apparent from the following description, drawings, and claims.

SUMMARY OF THE INVENTION

The invention features a method and test cell for the detection of a preselected ligand in a liquid sample such as a body fluid.

The test cell useful in the practice of the invention has an elongate outer casing which houses an interior permeable material, e.g., glass fiber, capable of transporting an aqueous solution by capillary action, wicking, or simple wetting. The casing defines a sample inlet, and interior regions which, for ease of description, can be designated as a test volume and a reservoir volume. The reservoir volume is disposed in a section of the test cell spaced apart from the inlet; and preferably is filled with sorbent material. The reservoir acts to receive liquid transported along a flow path defined by the permeable material and extending from the inlet and through the test volume. In the test volume is a test site comprising a first protein having a binding site specific to a first epitope of the ligand immobilized in fluid communication with the flow path, e.g., bound to the permeable material or to latex particles entrapped in or bonded to the permeable material. A window such as a hole or transparent section of the casing permits observations of the test site through the casing wall.

In a preferred embodiment, the flow path is restricted or narrowed in the test area, thereby channeling and concentrating fluid flow into contact with the test site. It is also preferred that the test cell include a solution filtering means disposed in the flow path between the sample inlet and the test site. The filtration means can comprise a separate, conventional filter element disposed within the casing of the test cell in fluid communication with the permeable material defining the flow path, but preferably is defined simply by a portion of the permeable material itself. The provision of such a filtration means in the test cell has the effect of removing by entrapment from impure samples, such as urine samples, a portion of the particulates and nonspecific interfering factors which sometimes cause false positive readings.

The method of the invention requires the use of a conjugate comprising a second protein bound to colored particles such as a metal sol or colloid, preferably gold. The conjugate can take two distinct forms, depending on whether the assay is designed to exploit the "sandwich" or "competitive" technique.

In the case of the sandwich technique, the second protein comprises a site which binds to a second epitope on the ligand. This type of conjugate reacts with the ligand to form a complex in the liquid sample. The complex is detected by visual observation of color development at the test site in the test cell. At the test site, the ligand bound with the conjugate reacts with the immobilized first binding protein to form a "sandwich" of the first protein, ligand, second protein, and colored particles. This sandwich complex is progressively produced at the test site as sample continuously passes by, filling the reservoir. As more and more conjugate is immobilized, the colored particles aggregate at the test site and become visible through the window, indicating the presence of ligand in the liquid sample.

In the case of the competitive technique, the second protein binds with the first protein in competition with the ligand. The second protein comprises, for example, an authentic sample of the ligand or a fraction thereof which has comparable affinity for the first protein. As the liquid sample is transported in contact with the test site, ligand, if any, and the conjugate compete for sites of attachment to the first protein. If no ligand is present, colored particles aggregate at the test site, and the presence of color indicates the absence of detectable levels of ligand in the sample. If ligand is present, the amount of conjugate which binds at the test site is reduced, and no color, or a paler color, develops.

In one embodiment of the invention, the test liquid is mixed with the conjugate outside the test cell. In another embodiment, the conjugate is disposed in freeze-dried or other preserved form on the permeable material between the inlet and the test site, and the sample liquid resolubilizes the conjugate as it passes along the flow path.

Color development at the test site may be compared with the color of one or more standards or internal controls to determine whether the development of color is a true indication of the presence or absence of the ligand, or an artifact caused by nonspecific sorption.

In one embodiment employing the sandwich technique, the standard consists of a negative control site, preferably disposed adjacent the test site, and visible through a second window proximate the first. The negative control site preferably is prepared identically to the test site, except immobilization of the first binding protein is omitted. Therefore, although the conjugate will reach the control Site, it aggregates due only to non-specific binding. If the test site is not appreciably more intense in color than the control site, the assay is considered negative.

In another embodiment, the assay and test cell may include a positive control. Thus, when exploiting the sandwich technique, the cell may have an authentic sample of the ligand immobilized at a control site. If no color develops at this control site, the assay is considered inconclusive. When exploiting the competitive technique, the development of color at the positive control site means the assay results are inconclusive.

Broadly, the method of the invention involves the use of a test cell of the type described above to achieve an easily readable, sensitive, reproducible indication of the presence of a ligand, e.g., human chorionic gonadotropin (hCG), in a test sample such as a human urine sample. The method involves the step of transporting the sample and a conjugate comprising a protein bound to a metal sol or other colored particle along a flow path and in contact with a test site comprising immobilized binding protein specific to an epitope of the ligand, and preferably also in contact with a control site. Preferably, the colored particle comprises a gold sol; the flow path in the region of the test site is reduced in cross-section relative to other parts of the flow path; the sample is passed through a filtration means after it enters the test cell but before it contacts the test site; and the test site comprises latex particles entrapped or otherwise fixed in the flow path having the immobilized protein on their surface. In the practice of the process, either the conjugate is premixed with the sample, or the conjugate is disposed in preserved form, e.g., lyophilized, in the flow path between the inlet and the test site. In either case, placement of the test cell in the sample, or application of the sample to the inlet, initiates flow, and the result is read by observing color development at the test site, or by comparing the color of the test site and control site.

The use of the colored particle detection system in combination with the filtration means, the concentrating effect of flow of the sample, and the ease of comparison between the colors of the test and control sites, together enable construction of a family of extremely sensitive assay systems which minimize false positives and can be used effectively by untrained persons.

BRIEF DESCRIPTION OF THE DRAWING

FIG. 4A is a cross-sectional, top view of the test cell of FIG. 3;

FIG. 4B is a cross-sectional, side view of the test cell of FIG. 3 taken at line 4B—4B of FIG. 4A;

FIG. 5 is a cross sectional view of the cell of FIG. 3 taken at line 5—5 of FIG. 4B.

Like reference characters in the respective drawn figures indicate corresponding parts.

DESCRIPTION

Figure 1:
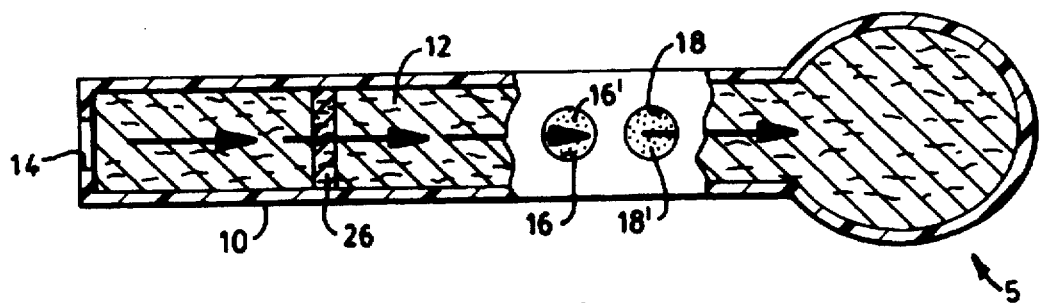
FIG. 1 is a cut-away, schematic, top view of an embodiment of a test cell useful in explaining the test cell and process of the invention.

The invention provides a test cell for conducting a sandwich or competitive immunoassay, and a process which utilizes the test cell and a conjugate comprising colored particles. As disclosed below, various features of the process and test cell of the invention cooperate to enable untrained personnel reliably to assay a liquid sample for the presence of extremely small quantities of a particular ligand while avoiding false positives and simplifying test procedures. The invention is ideal for use in over-the-counter assay test kits which will enable a consumer to self diagnose, for example, pregnancy, venereal disease, and other disease, infection, or clinical abnormality which results in the presence of an antigenic marker substance in a body fluid, including determination of the presence of metabolites of drugs or toxins. The assay process and the cell are engineered specifically to detect the presence of a preselected individual ligand present in a body or other fluids.

Broadly, the test cell and process of the invention can be used to detect any ligand which has heretofore been assayed using known immunoassay procedures, or known to be detectable by such procedures, using polyclonal or monoclonal antibodies or other proteins comprising binding sites for ligands. Various specific assay protocols, reagents, and analytes useful in the practice of the invention are known per se, see, e.g., U.S. Pat. No. 4,313,734, columns 4–18, and U.S. Pat. No. 4,366,241, columns 5–40.

The combination of features believed to be responsible for the excellent sensitivity and reproducibility of assays constructed in accordance with the invention is the use of the novel test cell which serves to concentrate ligand from a test sample at a test site in the cell, and the use of a metal sol or other colored particle as a marker system which permits direct visual observation of color development. False positives are reduced while maintaining excellent sensitivity by including in the test cell a negative control or control site whose color is compared with the test site, and by including a filtration means which limits the introduction to the test site of contaminants from the sample.

The assay is conducted by simply placing the inlet of the test cell in contact with a liquid test sample. One then merely waits for the test sample to pass through the cell and into reactive contact with the test site (and optionally one or more control sites) visible through a window or windows in the cell's exterior casing. In one embodiment, the conjugate is mixed with the sample and incubated briefly before the test cell is inserted. In another embodiment, the conjugate is disposed in preserved form in the flow path within the cell. If the ligand is present in the sample, it passes through the inlet and the interior of the cell along the flow path past the test and control sites, where, in the sandwich embodiment, it reacts with immobilized binding protein, e.g., antibody, at the test site, and perhaps also non-specifically at the control site. A "sandwich" forms at the test site comprising immobilized binding protein-ligand binding protein-colored particle. The presence of the sandwich complex and thus the ligand is indicated by the development of color caused by aggregation of the metal sol particles at the test site. A deeper color at the test site than at the negative control site is a positive indication of the presence of the ligand.

By providing a reservoir of sorbent material disposed beyond the test and control sites, a relatively large volume of the test liquid and any ligand it contains can be drawn through the test area to aid sensitivity. Optionally, the region of the flow path in the test cell defining the test and control sites is restricted in cross-sectional area relative to other regions of the flow path. This feature produces a "bottleneck" effect wherein all ligand in the entire volume of sorbent sample must pass through the restricted flow area immediately about the test site where it will be immobilized by reaction with binding protein.

From the foregoing, it will be apparent that the success of the test procedure is dependent on ligand present in the sample reacting with the conjugate, or on reproducible competition between the ligand and the conjugate for sites of attachment at the test site. In accordance with the invention, as noted above, the assays can be conducted by premixing the conjugate with the liquid sample prior to introduction into the elongate test cell. Alternatively, the conjugate may be disposed in preserved form, e.g., freeze-dried, in the flow path within the test cell upstream of the test and control sites. In this case, the cell is placed directly in the liquid sample solution without premixing. Ligand, if any, passing up through the cell and entrained within the liquid moves into contact with the conjugate forming an immune complex or initiating competition in situ as flow continues. This latter technique has the advantage that it eliminates a manipulative step in the assay procedure, and accordingly a possible source of error.

Figure 2:
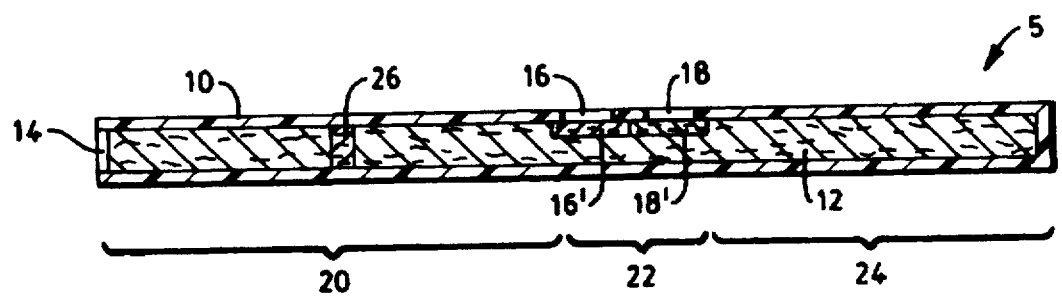
FIG. 2 is a cross-sectional side view of the test cell of FIG. 1.

Referring to the drawing, FIGS. 1 and 2 illustrate schematically an embodiment of a test cell 5 constructed in accordance with the invention useful in explaining its principles of construction. It comprises an outer, molded casing 10 which defines a hollow, elongate enclosure filled with a permeable, sorbent material 12. Casing 10 also defines a test liquid inlet 14 and a pair of circular openings 16, 18 comprising windows through which sorbent material 12 is visible.

Sorbent material 12 and the interior of casing 10 together define a flow path passing generally from left to right in FIGS. 1 and 2. When the test cell is placed with inlet 14 disposed within or otherwise in contact with a liquid sample, the liquid is transported by capillary action, wicking, or simple wetting along the flow path through downstream flow section 20, test volume 22, and into reservoir volume 24, generally as depicted by the arrows. The flow section 20 of the flow path disposed inwardly of the inlet 14 serves as a filter which can remove from impure test samples particulate matter and interfering factors. The provisions of such a filtration means 20 downstream of the inlet 14 is believed to contribute to the success of the system and its ability to avoid false positives.

Disposed within sorbent material 12 is a band 26 of dehydrated conjugate, e.g., antibody-metal sol. As the liquid sample moves past band 26, the conjugate is entrained in the liquid, reconstituted, and reacts or competes with ligand, if present, dissolved in the liquid sample. Of course, conjugate band 26 may be eliminated, and the conjugate added to the test liquid prior to introduction of the cell 5 as previously noted.

Within the volume of sorbent material 12 disposed directly beneath circular openings 16 and 18 in casing 10 is disposed, respectively, control site 16' and test site 18'. In the drawing, the control and test site are illustrated as being disposed serially along the flow path. Alternatively, the control and test site or sites may be disposed side by side or in other spacial relationships.

Test site 18' comprises a preselected quantity of antibody against an epitope of the ligand to be detected immobilized in place within the flow path. Its detailed chemical structure can vary widely. Control site 16' is preferably identical in size and chemical makeup to test site 18', excepting that the immobilized antibody present at the test site 18' is omitted at the control site 16'. Thus, any nonspecific aggregation of, e.g., ligand-conjugate or free conjugate, which occurs at test site 18' also will occur at control site 16'. A deeper color at test site 18' as compared with control site 16' is a positive indication of ligand in the sample in the sandwich assay.

The invention is not limited by the precise nature of the test site 18' and corresponding control site 16', and in fact, control site 16' may be entirely eliminated if a reduction in sensitivity can be tolerated. Generally, antibody or other binding protein may be immobilized at test site 18' using adsorption, absorption, or ionic or covalent coupling, in accordance with methods known per se. A currently preferred formulation for test site 18' is to immobilize monoclonal antibody against an epitope of the ligand on latex beads, and then to entrap or otherwise link the beads in sorbent material 12 at region 18'. Control site 16' is fabricated identically, except that the latex beads contain non specific immunoglobulin, e.g., immunoglobulin from bleedings from an animal that has not been immunized.

Disposed beyond test volume 22 is a reservoir volume 24 comprising a relatively large mass of sorbent or supersorbent material. The purpose of reservoir volume 24 is to assure that a reasonably large amount of test liquid is drawn through test volume 22. Increasing the volume of reservoir 24 can have the effect of increasing the sensitivity of the assay procedure, as it results in an increase in the amount of ligand passing through the test area 22. Suitable sorbents include commercial materials of the type available, for example, from The Dow Chemical Company of Midland, Mich., and the Chemical division of American Colloid, Arlington Heights, Ill. These materials can absorb many times their weight in water and are commonly used in disposable diapers. They comprise lightly crosslinked polyacrylate salts, typically alkali metal salts.

Polyclonal antisera and indeed monoclonal antibodies or fractions thereof having specific binding properties and high affinity for virtually any antigenic substance are known and commercially available or can be produced from stable cell lines using well known cell fusion and screening techniques. The literature is replete with protein immobilization protocols. See, for example, *Laboratory Techniques in Biochemistry and Molecular Biology*, Tijssen, Vol. 15, Practice and Theory of Enzyme immunoassays, chapter 13, The Immobilization of Immunoreactants on Solid Phases, pp. 297–328, and the references cited therein.

Metal sols and other types of colored particles useful as marker substances in immunoassay procedures are also known per se. See, for example, U.S. Pat. No. 4,313,734, Feb. 2, 1982, to Leuvering, the disclosure of which is incorporated herein by reference. For details and engineering principles involved in the synthesis of colored particle conjugates see Horisberger, Evaluation of Colloidal Gold as a Cytochromic Marker for Transmission and Scanning Electron Microscopy, Biol. Cellulaire, 36, 253–258 (1979); Leuvering et al, Sol Particle Immunoassay, J. Immunoassay 1 (1), 77–91 (1980), and Frens, Controlled Nucleation for the Regulation of the Particle Size in Monodisperse Gold Suspensions, Nature, Physical Science, 241, pp. 20–22 (1973).

The cell can take, various forms. It will usually comprise an elongate casing comprising interfitting parts made of polyvinyl chloride, polypropylene, or other thermoplastic resin. Its interior flow path will contain a relatively inert material or a combination of materials suitable for transporting the liquid. In some circumstances it may be preferable to use a material of higher sorptivity as the reservoir, promoting the flow of liquid, and a different material for remaining portions of the flow path.

From the foregoing it should be apparent that the advantages in reproducibility, sensitivity, and avoidance of false positives of assay systems constructed in accordance with the invention are traceable to a combination of features of the invention. In use, the test cell of the invention and the metal sol particles used as a marker together cooperate to result in an increase in color intensity progressively as ligand complexed with conjugate is trapped at the test site by the immobilized binding protein. This approach can be utilized to design assays and test cells for essentially any antigenic material.

The invention will be further understood from the following non-limiting examples.

EXAMPLE 1

Figure 3:
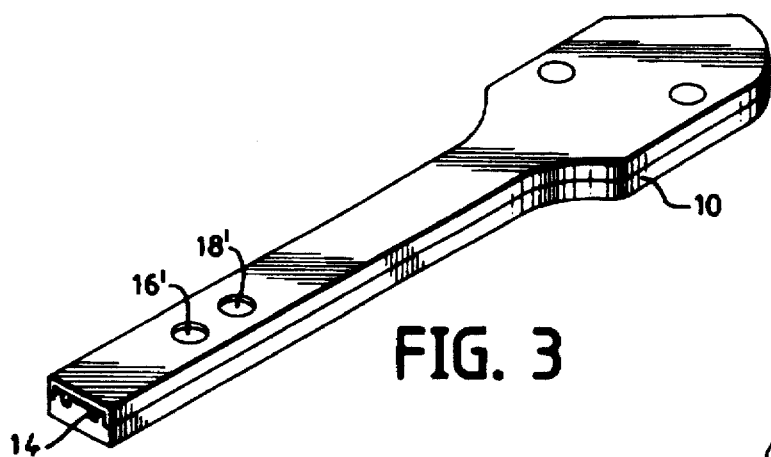
FIG. 3 is a perspective view of a currently preferred test cell constructed in accordance with the invention.
Figure 6:
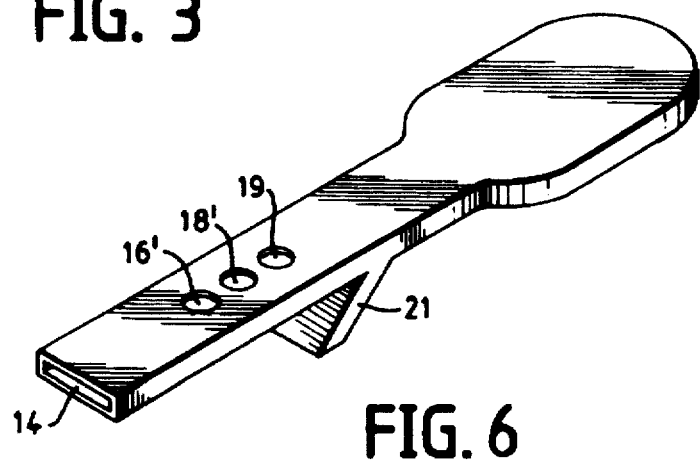
FIG. 6 is a perspective view of another embodiment of a test cell constructed in accordance with the invention.

The currently preferred test device embodying the invention is shown in FIGS. 3, 4A, 4B, and 5. A modification of the device depicted in FIG. 3 is shown in FIG. 6, and includes a second control site 19 in addition to control site 16' and test site 18', as well as a stand 21 useful for maintaining the test cell in an incline position with the reservoir downhill. When a test sample is applied to inlet 14, gravity as well as sorption aids in transporting the sample along the flow path.

As shown in FIGS. 3, 4A, 4B, and 5, the preferred test cell of the invention differs from the exemplary device discussed above and shown in FIGS. 1 and 2 in certain of its more specific internal features. Specifically, the casing 10 comprises a pair of interfitting polymeric parts including a U-shaped top part 10' which, when the device is assembled, interfits with lower part 10". Top and bottom parts 10' and 10" may be connected through a hinge region 11. The bottom section 10" defines a pair of channels 28 above which is disposed a strip of glass fiber paper 13 (available commercially from Eaton Dikeman, Grade 111, or Whatman, Grade GFA). Test liquid applied through inlet 14 soaks along the paper strip 13 which defines the flow path and a filtering means region 20, as well as a positive control site 16' and test site 18' visible through windows 16 and 18 consisting of openings through upper mating member 10'. The paper strip 13 overlaps into reservoir volume 24, which is defined by a cavity between the interfitting top and bottom mating members 10' and 10". The cavity in this case is filled with sorbent blotting paper 12 comprising the sorbent reservoir. A suitable paper is sold as Grade 12A absorbent paper, a cellulose product available from Schleicher and Schuell. In one preferred embodiment, the dimensions of the glass fiber paper 13 were approximately one quarter inch by three inches, and those of the absorbent material 12 approximately two inches by five thirty seconds of an inch on each side. A number of these devices were produced and further treated to adapt them to detect pregnancy by assay of urine.

Test site 18' in each device was fabricated as a spot within fiber paper 13 using the following technique. Latex beads available commercially and comprising polystyrene particles 0.3 micron in diameter were passively coated with purified rabbit anti-human chorionic gonadotropin. The polyclonal antibody was purified using conventional techniques from bleedings of a rabbit previously immunized with human chorionic gonadotropin in a manner know per se. Equal parts of a latex (0.6% by weight) having a continuous phase of glycine buffer, pH=8.3, and a 1 mg/ml antibody solution in the same buffer were mixed and incubated at 37° C. 15 microliters of this solution, comprising approximately 0.6% solids, were added, one drop at a time, to the glass fiber paper 13 to produce spot 18' after the devices had been assembled. The spots were then allowed to dry at 37° C. The control site 16' was produced identically to the test site disclosed immediately above, excepting that rabbit polyclonal non-immune gamma globulin was used in place of the anti-hCG gamma globulin.

Metal sol particles were prepared in accordance with the method of Frens, Controlled Nucleation for the Regulation of the Particle Size in Mono Dispersed Gold Solutions (1973), supra. Briefly, the gold sol was prepared by reducing a 4% solution of gold chloride with 1% sodium citrate to produce gold particles of approximately 18 nm in diameter. The particles were made immunochemically reactive by admixture with a monoclonal antibody specific for human chorionic gonadotropin with no detectable cross-reactivity with human leutinizing hormone. The antibody was purchased from Charles River Labs, and is produced using standard techniques including purification from ascites using HPLC ion exchange chromatography. It was added to the gold sol as a 10 ug/ml solution in borate buffer, pH-6. The bound antibody fraction is separated from the free fraction by either density centrifugation or gel filtration chromatography. Additional details of the currently preferred procedure for making the antibody sol conjugate are disclosed by Leuvering et al, J. Immunoassay (1980) supra. Individual batches of the latex and the conjugate are titrated to optimize activity so that a suitable amount of latex is applied to the test site and a suitable amount of conjugate is used in conducting the test.

Test Protocol

To a 10×50 mm test tube of lyophilized gold sol antibody conjugate is added 0.5 ml urine sample containing a known quantities of hCG. The samples comprised hCG standards purchased from Sigma Chemical Company diluted in processed, hCG negative urine. The contents of the tube are mixed by shaking in a horizontal motion until the lyophilized antibody is dissolved. The device depicted in FIGS. 3–5 is then inserted into the tube, and the results are read after the entire fluid volume has been absorbed.

The results of this qualitative procedure are as follows:

| mIU hCG | Color of Control Spot | Color of Reagent Spot |
|---|---|---|
| 0 | grey | grey |
| 25 | grey | pink hue |
| 50 | grey | pink |
| 100 | grey | rose |
| 150 | grey | rose |
| >150 | grey | dark rose |

The pink color clearly visible at 50 mIU of human chorionic gonadotropin means that the test can detect pregnancy one day after a missed menstrual period. In initial stages of testing, approximately 50 negative samples from various sources have been run with no false positives or even border-line cases. It is anticipated that the commercial device will have less than 1% false positives.

Non-limiting examples of materials which may be assayed in accordance with the invention in addition to the human chorionic gonadotropin noted above include human leutinizing hormone, progesterone, estrogen, and streptococcus.

Other embodiments are within the following claims.

What is claimed is:

1. A method of detecting a ligand in a liquid sample suspected of containing said ligand, the method comprising the steps of:

(a) providing a test strip, disposed within a housing, comprising sorbent material and defining a flow path, a sample inlet and, spaced apart from said inlet in said flow path,
a test site having immobilized thereon a first protein having a binding site specific for a first epitope on said ligand and a separate control site;

(b) providing a conjugate comprising colored particulate material coupled to a second protein having a binding site specific for a second epitope on said ligand;

(c) applying to said inlet said liquid sample;

(d) transporting to said test site and said control site by sorption, capillary action, wicking, or wetting along said flow path said liquid sample in admixture with said conjugate thereby to produce, at said control site, color indicative of a valid test result and indicative that conjugate has bound specifically or non-specifically at said control site, and at said test site, of said ligand is present in said liquid sample, a specific binding reaction product comprising said ligand and an aggregate of said colored particulate material to produce a color visible to the unaided eye indicative of the presence of said ligand.

2. The method of claim 1 wherein said flow path further comprises a filtration means disposed between said inlet and said test site and said step (d) further comprises:

filtering said liquid sample through said filtration means prior to said liquid sample contacting said test site.

3. The method of claim 1 wherein said control site is downstream of said test site and comprises binding protein which specifically binds conjugate.

4. The method of claim 1 further comprising the step of mixing said conjugate with said liquid sample to form the admixture of step (d) prior to applying said liquid sample to said inlet.

5. The method of claim 1 wherein a solution consisting essentially of said conjugate is applied at a location in said flow path upstream of said test site and dried on said test strip prior to step (c), said method further comprising the step of transporting said liquid sample into contact with said dried conjugate prior to contact with said test site.

6. The method of claim 1 wherein said first and second proteins are antibodies and at least one of said antibodies is a monoclonal antibody.

7. The method of claim 1 wherein said first protein has binding site specific to an epitope of human chorionic gonadotropin (hCG) and said ligand is hCG.

8. A method of claim 1 wherein said first protein has a binding site specific to an epitope of human progesterone and said ligand is progesterone.

9. A method of detecting a ligand in a liquid sample suspected of containing said ligand, the method comprising the steps of:

(a) providing a test strip, disposed within a housing, comprising sorbent material and defining
a flow path,
a sample inlet, and, spaced apart from said inlet in said flow path,
a test site having immobilized thereon a first protein having a binding site specific for a first epitope on said ligand, and
a separate control site;

(b) providing a conjugate comprising a metal sol particle coupled to a second protein having a binding site specific for a second epitope on said ligand;

(c) applying to said inlet said liquid sample; and (d) transporting to said test site and said control site by sorption, capillary action, wicking or wetting along said flow path said liquid sample in admixture with said conjugate, thereby to produce, at said control site, color indicative of a valid test result and indicative that conjugate has bound specifically or non-specifically at said control site, and at said test site, if said ligand is present in said liquid sample, a specific binding reaction product comprising said ligand and an aggregate of said metal sol particle to produce a color visible to the unaided eye indicative of the presence of said ligand.

10. A method of detecting a ligand in a liquid sample suspected of containing said ligand, the method comprising the steps of:

(a) providing a test strip, disposed within a housing, comprising sorbent material and defining
a flow path,
a sample inlet, and, spaced apart from said inlet in said flow path,
a test site having immobilized thereon a first protein having a binding site specific for a first epitope on said ligand,
a separate control site, and disposed in said flow path upstream of said test site,
a dried reagent consisting essentional of a conjugate comprising colored particulate material coupled to a second protein having a binding site specific for a second epitope on said ligand;

(b) applying to said inlet said liquid sample; and (c) transporting by sorption, capillary action, wicking or wetting along said flow path said liquid sample into contact with said dried conjugate to produce an admixture of said liquid sample and said conjugate, and thereafter transporting said admixture into contact with said test site and said control site thereby to produce, at said control site, color indicative of a valid test result and indicative that conjugate has bound specifically or non-specifically at said control site, and at said test site, if said ligand is present in said liquid sample, a specific binding reaction product comprising said ligand and an aggregate of said colored particulate material to produce a color visible to the unaided eye indicative of the presence of said ligand.

\* \* \* \* \*